United States Patent
Schmit et al.

(10) Patent No.: US 8,673,832 B2
(45) Date of Patent: Mar. 18, 2014

(54) LIQUID SKIN CLEANSER WITH MULTIPLE SIGNALS OF ADEQUATE WASH DURATION WITH ADEQUATE MECHANICAL FORCE

(75) Inventors: Catherine Schmit, Glendale, AZ (US); James J. Dalton, Scottsdale, AZ (US); Heidi B. Goldfarb, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 736 days.

(21) Appl. No.: 12/069,640

(22) Filed: Feb. 12, 2008

(65) Prior Publication Data

US 2009/0054286 A1   Feb. 26, 2009

Related U.S. Application Data

(60) Provisional application No. 60/966,091, filed on Aug. 24, 2007.

(51) Int. Cl.
*C11D 3/40* (2006.01)
*A61Q 5/02* (2006.01)

(52) U.S. Cl.
USPC .......................................... 510/100; 510/123

(58) Field of Classification Search
USPC ................................................. 510/123, 100
See application file for complete search history.

(56) References Cited

U.S. PATENT DOCUMENTS

| | | | | |
|---|---|---|---|---|
| 5,861,440 | A | * | 1/1999 | Gohla et al. .................. 514/738 |
| 6,924,256 | B2 | * | 8/2005 | Massaro et al. ............... 510/119 |
| 2004/0228886 | A1 | * | 11/2004 | Ding et al. ..................... 424/401 |
| 2006/0029625 | A1 | * | 2/2006 | Niebauer ...................... 424/401 |
| 2006/0127425 | A1 | * | 6/2006 | Walls et al. ................... 424/401 |

* cited by examiner

*Primary Examiner* — Ling Choi
*Assistant Examiner* — Thuy-Ai Nguyen
(74) *Attorney, Agent, or Firm* — David K. Benson

(57) ABSTRACT

A personal cleansing composition includes a carrier, and a first plurality of beads entrained in the carrier. The beads impart, to a user applying the cleansing composition with hand rubbing force, perceivable tactility for a limited predetermined duration that corresponds to a minimum adequate cleansing time period. In accordance with another embodiment of the present invention, the personal cleansing composition further includes a second plurality of beads entrained in the carrier. The second plurality of beads imparts to the user a perceivable change in color for the cleansing composition for a second limited predetermined duration that is substantially equal to the duration that the tactility imparted by the first plurality of beads is perceivable to the user.

25 Claims, 1 Drawing Sheet

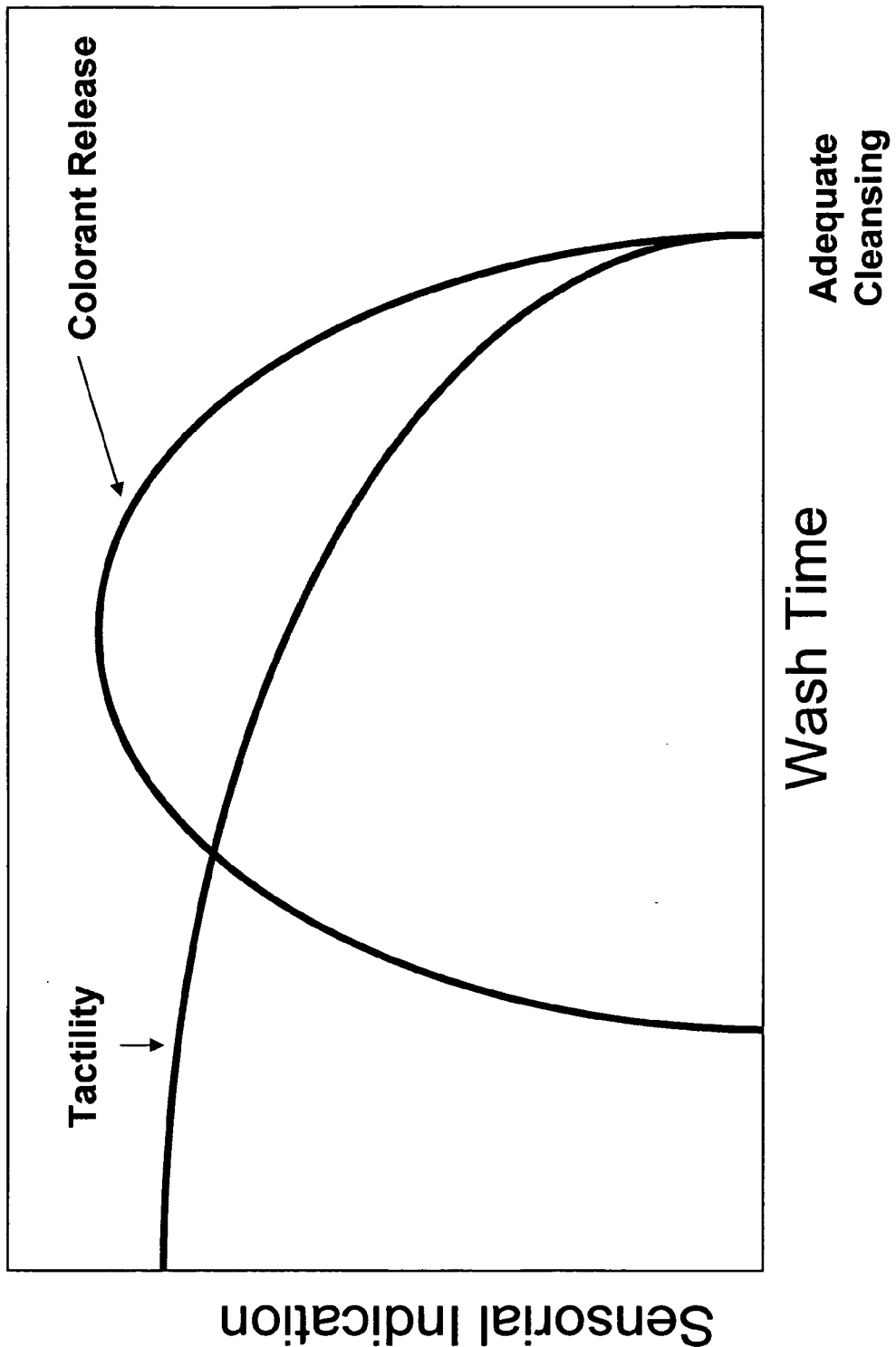

LIQUID SKIN CLEANSER WITH MULTIPLE SIGNALS OF ADEQUATE WASH DURATION WITH ADEQUATE MECHANICAL FORCE

CROSS-REFERENCES TO RELATED APPLICATIONS

The present application claims the benefit of U.S. Provisional Application No. 60/966,091, filed Aug. 24, 2007, which is herein incorporated in its entirety by reference.

FIELD OF INVENTION

The present invention is directed to a personal cleansing composition. More particularly, the present invention is directed to a cleansing composition that is adapted to provide signals to encourage a person using the composition to wash until proper cleansing has occurred.

BACKGROUND

Cleansing compositions such as body washing agents typically include a carrier system that may have conventional perceivable sensorial attributes. Efforts are continually made to make the sensorial attributes of cleansing compositions appealing to users. Fragrances, colorants, temperature change imparting agents (both endothermic and exothermic), and tactility modifying agents are just a few examples of components that provide sensorial attributes to cleansing compositions to induce consumers to purchase and use particular compositions. However, such components are not typically adapted with a view toward improving cleaning efficacy. In other words, cleansing components and agents that provide sensorial attributes to compositions are typically considered separately when developing and implementing cleansing formulations. Consequently, conventional perceived sensorial attributes of a composition are not usually coupled or coordinated with particular hand washing events in a manner that increases the probability that a user will comply with proper body cleansing requirements.

A few recent developments reflect efforts by some to produce cleansing compositions that tie the concepts of sensorial attributes with adequate cleansing. For example, WO 2004/052307 discloses hand and hair cleaning compositions that include a carrier, and a plurality of capsules within the carrier. The capsules contain and, while washing using the cleaning composition, release a material that provides a sensorial stimulus. The capsules are adapted to release the material at a particular time that is coincident with a discrete event such as lapse of an adequate hand cleaning time. Some materials that may be contained in the capsules are colorants or fragrances that, when seen or smelled by the user, indicate that the discrete event has occurred. Other materials that may be contained in the capsules are pH modifiers that, when released, change the alkalinity or acidity of the carrier, and consequently change the perceived color of the overall composition. Yet another material that may be contained in the capsules is an acidic component that, when released, reacts with an alkaline carrier and produces bubbles and an audible sound, along with a tactile sensation corresponding to the bubble formation.

One limitation of the prior art cleaning solutions is that users are likely to discontinue washing as soon as any sensorial indicia are produced. This is particularly a problem when the sensorial indicia include color changes produced by release of colorants from a capsule or other bead included in a carrier solution. If a consumer discontinues scrubbing as soon as a color change is perceived, then rinsing the cleansing solution will cause several intact beads to fall into a sink or other surface, and collapsing of the beads will produce smears or other messy residue. Accordingly, there is a need for personal cleansing compositions that provide sensorial indicia that indicate adequate washing to a user. There is also a need for such compositions that ensure the usage of substantially all of the sensorial indicia before a user rinses the cleansing composition.

SUMMARY OF THE INVENTION

This summary of the invention section is intended to introduce the reader to aspects of the invention. Particular aspects of the invention are pointed out in other sections herein below, and the invention is set forth in the appended claims which alone demarcate its scope.

In accordance with an exemplary embodiment of the present invention, a personal cleansing composition is provided. The composition includes a carrier, and a first plurality of beads entrained in the carrier. The beads impart, to a user applying the cleansing composition with hand rubbing force, perceivable tactility for a limited predetermined duration that corresponds to a minimum adequate cleansing time period.

In accordance with another exemplary embodiment of the present invention, the personal cleansing composition further includes a second plurality of beads entrained in the carrier. The second plurality of beads imparts to the user a perceivable change in color for the cleansing composition for a second limited predetermined duration that is substantially equal to the duration that the tactility imparted by the first plurality of beads is perceivable to the user.

BRIEF DESCRIPTION OF THE DRAWINGS

FIG. 1 is a graph depicting sensorial intensity provided to a user applying a hand rubbing force to beads included in a cleansing composition during a washing event, and correlates the sensorial intensity with the duration of the washing event.

DETAILED DESCRIPTION OF THE INVENTION

The detailed description of various exemplary embodiments of the invention herein makes reference to exemplary compositions and methods of process for producing such compositions. While these exemplary embodiments are described in sufficient detail to enable those skilled in the art to practice the invention, it should be understood that other embodiments may be realized, and that logical and processing changes may be made without departing from the spirit and scope of the invention. Thus, the detailed description herein is presented for purposes of illustration only and not of limitation.

According to one embodiment, a cleansing composition includes a carrier with a first plurality of beads entrained therein. The beads imparting perceived tactility to a user applying the cleansing composition with a hand rubbing force. The tactility is perceivable by the user for a limited predetermined duration that corresponds to a minimum adequate cleansing time period. The beads are preferably formed as a uniform composition that is adapted to disintegrate after adequate cleansing occurs to the extent that the beads no longer impart perceivable tactility to the user.

The bead-containing cleansing compositions of the present invention are primarily contemplated for use as personal cleansing agents. However, other bead-containing cleansing compositions that impart perceived tactility to the user and that employ the principles of the present invention may be adapted for functions other than personal cleansing. When used for personal cleansing, the compositions may be useful as agents for washing human skin, hair and/or nails. The cleansing compositions may be included in various formulations including liquids, creams, gels, foams, lotions, mousses, and powders, to name a few examples.

The beads are included in a suitable carrier, which includes aqueous and/or water-miscible solutions in which the beads of the present inventions can be maintained without substantial degradation during non-use of the cleaning composition. According to a preferred embodiment, the carrier is aqueous and includes at least about 50% water by weight. Other alcohol-based carriers that may also be useful in combination with water include, as just a few examples, various aliphatic straight and branched alcohols, glycols, and alcohols of polyethers.

The compositions in accordance with the invention also include at least one surfactant for the purpose of forming homogenous solutions or for dispersion or suspension of components for the purpose of creating a heterogenous system such as an emulsion or suspension. The plurality of surfactants may include anionic, cationic, nonionic, and/or amphoteric surfactants. Some exemplary anionic surfactants include sodium laureth sulfate, sodium toluene sulfonate, and sodium naphthalene sulfonate. Some exemplary cationic surfactants include alkyl, aryl, and alkyl aryl amines. Some exemplary nonionic surfactants include ethoxylates such as alkyl ethoxylates, aryl ethoxylates, alkyl aryl ethoxylates, fatty acid ethoxylates, and esters of such ethoxylates with other compounds. Amphoteric surfactants (also called zwitterionic surfactants) are those having a positive and negative charge within the same molecule and therefore are a blend of cationic and anionic. A common example is the class of betaine surfactants.

Included in some exemplary cleansing compositions are one or more cleansing agents and one or more antimicrobial agents, which include substances that kill or inhibit the growth of microbes such as bacteria, fungi, viruses, and parasites. According to an exemplary embodiment, the compositions include a surfactant as a cleansing agent, and an antibacterial compound such as triclosan as an antimicrobial agent. Numerous other cleansing agents and anticmicrobial agents are known and may be included in the compositions of the present invention.

Additional components in the cleaning composition may be added to further impart a desired texture, to adjust the composition density, to provide a fragrance, for chelation or suspension, to increase the composition's usable life, to add color, to modify the pH, and so forth. For example, in an exemplary embodiment the cleansing composition includes a suspending agent such as an acrylates copoloymer, a film forming agent such as a polyquaternium compound, or a humectant such as glycerin.

As previously discussed, the first plurality of beads that are included in the cleansing composition impart perceived tactility to a user applying the cleansing composition with a hand rubbing force, and the tactility is perceivable by the user for a limited predetermined duration that corresponds to a minimum adequate cleansing time period. Throughout the specification, the terms "adequate washing" and "adequate cleansing" refer to a washing or cleansing skin to the point at which transient contaminants are thoroughly removed from the skin surface. The limited predetermined duration is typically between about 10 and about 30 seconds. However, to ensure adequate cleaning, the limited predetermined duration is between at least 15 seconds, and is preferably at least 15 to 20 seconds as recommended by the Centers for Disease Control.

The beads included in the first plurality of beads are formed as a uniform composition. During a washing event, the hand rubbing force exerted by the user causes the beads to wear down and disintegrate. The beads are made from a structural material that is hydrated by water content in the cleansing composition. Although hydration of the structural material is an important consideration when tailoring the beads to have a predetermined tactility-imparting life, the beads require the hand washing mechanical force in order to break down within the adequate cleaning time. More particularly, the mechanical force provided by the user causes the beads to disintegrate until they no longer impart perceivable tactility to the user during the range of seconds corresponding to the adequate cleaning time.

To provide perceived tactility to a user until adequate cleansing is completed, the beads included in the first plurality of beads have an average diameter ranging between about 400 and about 1200 microns. Smaller beads will provide inadequate tactility to a user. Beads having larger average diameters will provide tactility to a user, but the tactility may be uncomfortable or otherwise undesirable for users. It is also desirable to have a large number of beads, and smaller beads enable incorporation of a high bead concentration. According to a preferred embodiment, the beads have an average diameter ranging between about 500 and about 900 microns.

The beads included in the first plurality of beads are at least in part formed from a structural material that imparts the perceivable tactility. Although numerous materials exist as structural materials, some beads may include a polymeric carbohydrate or derivative thereof, such as a sugar and a binder, as exemplary structural materials. Some useful sugars are cellulose, and ethers of cellulose or alkyl cellulose. Also, some useful binders are sugar alcohols, with mannitol being one example. It is within the purview of the present invention that any material may be used as a structural material as long as it is sufficiently hard to provide a perceivable tactility to a user, and that it is sufficiently frangible to disintegrate when subjected to normal hand washing force to the extent that the tactility is no longer perceived after adequate washing has taken place.

According to one exemplary embodiment, the tactile beads also impart, to a user applying the cleansing composition with hand rubbing force, a perceivable change in color to the cleansing composition. More particularly, the beads included in the first plurality of beads include a colorant that is released into the cleansing composition when subjected to the hand rubbing force. The color that the beads produce as they disintegrate during washing is not as important as the perceptibility of the cleansing composition color change. As previously mentioned, the tactile beads are formed as a uniform composition that disintegrates due to the hand rubbing force. Consequently, the color is introduced into the cleansing lather almost immediately after washing begins. Color is continuously released from the beads as they continue to disintegrate. Since the beads are adapted to be substantially completely disintegrated upon completion of the predetermined adequate washing period, in addition to no longer imparting perceivable tactility, the beads also no longer release additional color or impart additional color change once adequate washing has occurred.

Table 1 below provides an exemplary bead formulation for tactile beads that also include colorant, according to the embodiment in which the beads provide both perceivable tactility and color change. Of course, colorant may be omitted from the beads if it is desirable for the beads to only impart perceivable tactility.

TABLE 1

| Ingredient | BEAD A1 % (by weight) | BEAD A2 % (by weight) |
|---|---|---|
| Mannitol | 25-50 | >50 |
| Cellulose | 25-50 | 25-50 |
| Hydroxypropyl Methylcellulose | <1 | <0.1 |
| Ultramarine | 25-50 | 0 |
| Chromium Hydroxide Green | 0 | 10-15 |
| Magnesium Stearate | 5-10 | 5-10 |

Referring now to FIG. 1, a graph depicts sensorial intensity provided to a user applying a hand rubbing force to beads included in a cleansing composition during a washing event, and correlates the sensorial intensity with the duration of the washing event. The trace labeled "TACTILITY" represents the perceived sensorial intensity for the tactility imparted by the beads in the first set of beads. As illustrated in the graph, the tactility is perceived with a fairly constant intensity for most of the washing time, and then drops sharply as the beads reach complete disintegration at a point that corresponds to an adequate washing period. If colorant is included in the tactile beads, the same trace corresponds to the perceived release of color since the beads are a substantially uniform composition. The colorant is released with at a fairly constant rate for most of the washing time, and the cleansing composition grows increasingly more colorful. Then, the release rate of the colorant drops sharply as the beads reach complete disintegration at a point that corresponds to an adequate washing period. As a user notices that the cleansing composition is no longer darkening or becoming more colorful, the user also recognizes the lack of tactility imparted by the beads. Both the tactile and color indicia signal to the user that adequate cleansing has occurred.

According to another embodiment of the invention, two types of beads are incorporated into the cleansing composition. Beads of the first type are the tactility-imparting beads that may or may not include a colorant as discussed previously. The second plurality of beads are also entrained in the carrier and further impart, to the user applying the cleansing composition with hand rubbing force, perceivable change in color for the cleansing composition. More particularly, the beads included in the second plurality of beads include a colorant that is released into the cleansing composition when subjected to the hand rubbing force to impart the perceivable change in color. However, the change in color is perceived by the user in a different manner than that of the tactility-imparting beads that include a colorant. This is because instead of having a uniform composition, the beads included in the second plurality of beads include a coating that delays release of the colorant into the cleansing composition. Furthermore, the beads included in the second plurality of beads are adapted to release most of the colorant into the cleansing composition prior to the minimum adequate cleansing time period. Hereinafter, the beads included in the second plurality of beads will be referred to as "color beads."

Returning to FIG. 1, the graph also includes a trace labeled "COLORANT RELEASE" that corresponds to the rate at which colorant is released from the color beads into the cleansing composition, and therefore the change in color perceived by the user. The coating on the color beads delays release of colorant until washing has taken place for several seconds. When the coating breaks due to the hand rubbing force, the colorant initially produces perceivable streaks of color as the hands move back and forth, and the color then mixes into the cleansing composition. The color beads have similar coating thicknesses, and consequently release colorant to produce the perceivable streaks at about the same time, which explains the sharp rise and fall of the corresponding trace in FIG. 1. The color beads are adapted to be substantially completely broken, and to therefore release all the colorant contained therein, when adequate cleansing has occurred. Complete bead breakage by the all of the beads before rinsing prevents formation of a visibly messy bead debris or residue in a sink when the cleansing composition is rinsed from the user's body. According to an exemplary embodiment, the beads included in the second plurality of beads have more colorant than the first plurality of beads.

The color beads are made from a structural material that is hydrated by water content in the cleansing composition. As with the tactility-imparting beads, hydration of the structural material in the color beads is an important consideration when tailoring the beads to have a predetermined color-imparting life. The color beads require the hand washing mechanical force in order for the coating to break down within the adequate cleaning time. More particularly, the mechanical force provided by the user causes the color beads to break and release color until they no longer impart perceivable color streaks to the user during the range of seconds corresponding to the adequate cleaning time.

To provide perceived color release to a user until adequate cleansing is completed, the color beads have an average diameter ranging between about 400 and about 1200 microns. According to a preferred embodiment, the beads have an average diameter ranging between about 425 and about 1180 microns.

The color bead interior is at least in part formed from a structural material that is combined with colorant. Although numerous materials exist as structural materials, some beads may include a sugar and a binder as exemplary structural materials. Some useful sugars are cellulose, ethers of cellulose or alkyl cellulose, and lactose. It is within the purview of the present invention that numerous materials may be used as a structural material as long as it is sufficiently frangible to disintegrate when subjected to normal hand washing force. The color bead exterior is at least in part formed from a polymer or copolymer. Some useful coating materials that may form the color bead exterior include polyvinyl alcohol (PVA) and a copolymer of methyl vinyl ether and maleic anhydride (PVM/MA copolymer).

Table 2 below provides an exemplary bead formulation for color beads.

TABLE 2

| Ingredient | BEAD B1 % (by weight) | BEAD B2 % (by weight) |
|---|---|---|
| Cellulose | 15-20 | 15-20 |
| Hydroxypropyl Methylcellulose | 4-9 | 4-9 |
| Lactose | 25-32 | 25-32 |
| Ultramarine | 45-55 | 0 |
| Chromium Hydroxide Green | 0 | 45-55 |
| PVA | 0.1-2.0 | 0 |
| PVM/MA Copolymer | 0 | 1-4 |

We claim:
1. A cleansing composition, comprising:
a carrier; and a first plurality of beads, each formed as a uniform composition and having an average diameter ranging between about 400 and about 1200 microns, entrained in the carrier and immediately imparting; to a user applying the cleansing composition with hand rubbing force, perceivable tactility that is sustained for a limited predetermined duration of between about 15 and about 20 seconds and thereafter is substantially completely disintegrated and consequently no longer imparts perceivable tactility to the user applying the cleansing composition with hand rubbing force.

2. The cleansing composition according to claim 1, wherein the beads included in the first plurality of beads have an average diameter ranging between about 500 and about 900 microns.

3. The cleansing composition according to claim 1, wherein the beads included in the first plurality of beads comprise a structural material that imparts the perceivable tactility, the structural material comprising at least one polymeric carbohydrate or a derivative thereof.

4. The cleansing composition according to claim 3, wherein the at least one polymeric carbohydrate or derivative thereof is selected from the group consisting of cellulose, and ethers of cellulose or alkyl cellulose.

5. The cleansing composition according to claim 3, wherein the structural material further comprises a polyol binder.

6. The cleansing composition according to claim 1, wherein the beads included in the first plurality of beads further impart, to a user applying the cleansing composition with hand rubbing force, perceivable change in color for the cleansing composition.

7. The cleansing composition according to claim 6, wherein the beads included in the first plurality of beads comprise a colorant that is released into the cleansing composition when subjected to the hand rubbing force to impart the perceivable change in color.

8. The cleansing composition according to claim 7, wherein the beads included in the first plurality of beads are formed as a uniform composition that sufficiently disintegrates after the limited predetermined duration to no longer impart the perceivable change in color.

9. A cleansing composition, comprising:
a carrier;
a first plurality of beads, each formed as a uniform composition and having an average diameter ranging between about 400 and about 1200 microns, entrained in the carrier and immediately imparting, to a user applying the cleansing composition with hand rubbing force, perceivable tactility that is sustained for a limited first predetermined duration of between about 15 and about 20 seconds and thereafter is substantially completely disintegrated and consequently no longer imparts perceivable tactility to the user applying the cleansing composition with hand rubbing force; and
a second plurality of beads entrained in the carrier and including a colorant and imparting, to the user applying the cleansing composition with hand rubbing force, perceivable change in color for the cleansing composition by releasing the colorant into the cleansing composition for a second limited predetermined duration that is substantially within the duration that the tactility imparted by the first plurality of beads is perceivable to the user.

10. The cleansing composition according to claim 9, wherein the beads included in the second plurality of beads include a coating that delays release of the colorant into the cleansing composition.

11. The cleansing composition according to claim 9, wherein the beads included in the second plurality of beads are adapted to release most of the colorant into the cleansing composition prior to the minimum adequate cleansing time period elapsing.

12. The cleansing composition according to claim 9, wherein the beads included in the first plurality of beads further impart, to a user applying the cleansing composition with hand rubbing force, perceivable change in color for the cleansing composition.

13. The cleansing composition according to claim 12, wherein the beads included in the first plurality of beads comprise a colorant that is released into the cleansing composition when subjected to the hand rubbing force to impart the perceivable change in color.

14. The cleansing composition according to claim 13, wherein the beads included in the second plurality of beads have more colorant than the first plurality of beads.

15. The cleansing composition according to claim 13, wherein the beads included in the first plurality of beads are formed as a uniform composition that sufficiently disintegrates after the first limited predetermined duration to no longer impart the perceivable change in color.

16. The cleansing composition according to claim 9, wherein the beads included in the first plurality of beads are formed as a uniform composition that sufficiently disintegrates after the limited predetermined duration to no longer impart perceivable tactility to the user applying the cleansing composition with hand rubbing force.

17. The cleansing composition according to claim 9, wherein the beads included in the first plurality of beads have an average diameter ranging between about 500 and about 900 microns.

18. The cleansing composition according to claim 9, wherein the beads included in the second plurality of beads have an average diameter ranging between about 400 and about 1200 microns.

19. The cleansing composition according to claim 18, wherein the beads included in the second plurality of beads have an average diameter ranging between about 425 and about 1180 microns.

20. The cleansing composition according to claim 9, wherein the beads included in the first and second plurality of beads comprise a structural material, the structural material comprising a polymeric carbohydrate or derivative thereof.

21. The cleansing composition according to claim 20, wherein the beads included in the first plurality of beads further comprise a binder.

22. The cleansing composition according to claim 20, wherein polymeric carbohydrate or derivative thereof included in the structural material for the beads in the second plurality of beads includes at least one compound selected from the group consisting of cellulose, ethers of cellulose or alkyl cellulose, and lactose.

23. The cleansing composition according to claim 21, wherein the binder included in the first plurality of beads is a polyol.

24. The cleansing composition according to claim 9, wherein the cleansing composition has a total bead weight less than about 5%.

25. The cleansing composition according to claim 24, wherein the cleansing composition has a total bead weight less than about 1.2%.

* * * * *